United States Patent [19]

Swithenbank et al.

[11] 4,314,844
[45] Feb. 9, 1982

[54] HERBICIDAL SUBSTITUTED IMIDAZOLES

[75] Inventors: Colin Swithenbank, Perkasie; Ted T. Fujimoto, Warminster, both of Pa.

[73] Assignee: Rohm and Haas Company, Philadelphia, Pa.

[21] Appl. No.: 110,968

[22] Filed: Jan. 10, 1980

Related U.S. Application Data

[63] Continuation-in-part of Ser. No. 2,518, Jan. 11, 1979, abandoned.

[51] Int. Cl.³ .................. A01N 43/50; C07D 233/68; C07D 233/54
[52] U.S. Cl. ........................ 71/92; 548/337; 548/342; 548/137; 548/202; 546/278; 544/217; 544/215; 544/333; 544/224
[58] Field of Search .................... 548/337, 342; 71/92

[56] References Cited

U.S. PATENT DOCUMENTS

| 3,399,211 | 8/1968 | Sarrett et al. | 548/346 |
| 3,401,174 | 9/1968 | Woods et al. | 71/92 |
| 3,409,606 | 11/1968 | Lutz et al. | 548/337 |
| 3,443,015 | 5/1969 | Soper | 71/92 |
| 3,472,866 | 10/1969 | Newbold et al. | 71/92 |
| 3,501,286 | 3/1970 | Draber et al. | 71/92 |
| 3,691,178 | 9/1972 | Baldwin et al. | 424/250 |
| 3,707,475 | 12/1972 | Lombardino | 548/342 |
| 3,786,061 | 1/1974 | Novello et al. | 424/273 R |
| 3,818,014 | 6/1974 | Baldwin et al. | 424/273 R |
| 3,880,871 | 4/1975 | Haugwitz et al. | 548/337 |
| 3,952,005 | 4/1976 | Jorgensen | 424/273 R |
| 4,125,530 | 11/1978 | Baldwin et al. | 548/341 |
| 4,179,277 | 12/1979 | Beck et al. | 71/92 |

FOREIGN PATENT DOCUMENTS

| 2610527 | 9/1977 | Fed. Rep. of Germany | 548/337 |
| 6407401 | 1/1965 | Netherlands | 548/337 |
| 558913 | 8/1977 | U.S.S.R. | 548/337 |

OTHER PUBLICATIONS

Baldwin et al. II, J. Med. Chem. 1975, vol. 18 (9), pp. 895–900.

Primary Examiner—Henry R. Jiles
Assistant Examiner—Natalia Harkaway
Attorney, Agent, or Firm—Terence P. Strobaugh

[57] ABSTRACT

This invention relates to novel substituted imidazoles of the formula:

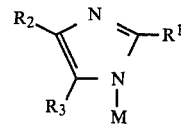

wherein
R¹ is a trifluoromethyl group, a halogen atom, an unsubstituted aryl group, a substituted aryl group, a heteroaromatic group, or a substituted heteroaromatic group;
$R^2$ and $R^3$ are selected from a hydrogen atom, a halogen atom and a trifluoromethyl group, provided $R^2$ and $R^3$ are not concurrently halogen; and
M is a hydrogen atom, an alkali or alkaline earth metal atom, a substituted carbonyl group, or other hydrolytically labile group.

These compounds and compositions containing them exhibit herbicidal activity. Fungicidal activity of compounds of the invention is also shown.

10 Claims, No Drawings

HERBICIDAL SUBSTITUTED IMIDAZOLES

This is a continuation-in-part of application Ser. No. 002,518 filed Jan. 11, 1979, now abandoned.

This invention relates to novel compounds which show activity as herbicides and fungicides, to novel herbicidal compositions which contain these compounds, and to new methods of controlling weeds with these herbicidal compositions.

Certain substituted imidazoles have been shown to be effective weed control agents. However, the herbicidal effectiveness of a given substituted imidazole cannot be predicted from an examination of the substituent groups attached to the ring and often quite closely related compounds will have quite different weed control abilities. The substituted imidazoles heretofore disclosed as herbicides are not completely effective. An ideal herbicide should give selective weed control, either pre- or post emergence which lasts for the full growing season without effect on subsequent crops. Alternatively, a strong need exists for total weed control either as a pre-planting aid in no-till agriculture or for rights-of-way etc., or leaf desiccation as a harvest aid. The known substituted imidazole herbicides fall short of these ideals, and it would thus be desirable to have new herbicides which show even more control of undesirable plants among desirable crop plants or which are most suitable for total weed control application.

In accordance with the present invention, there is provided a new class of substituted imidazoles having the formula

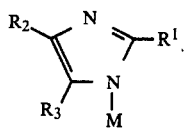

wherein $R^1$ is a trifluoromethyl group; a halogen atom, preferably bromine or chlorine; an unsubstituted aryl group, preferably phenyl; an aryl group, preferably phenyl, substituted with up to five substituents selected from a bromine atom, a chlorine atom, a fluorine atom, a trifluoromethyl group, a cyano group, a nitro group, a ($C_1$–$C_4$) alkyl preferably methyl group, a ($C_1$–$C_4$) alkoxy preferably methoxy group, a ($C_1$–$C_4$) alkylthio preferably methylthio group, a ($C_1$–$C_4$) alkylsulfonyl preferably methylsulfonyl group, a ($C_1$–$C_4$) alkylamino preferably methylamino group, and a ($C_1$–$C_4$) dialkylamino group, preferably a dimethylamino group; a 5 or 6 member heteroaromatic ring containing up to 3 heteroatoms selected from a nitrogen atom, a sulfur atom, and an oxygen atom; or a 5 or 6 member heteroaromatic ring fused with a second 5 to 6 member ring, with either ring containing up to 3 heteroatoms selected from a nitrogen atom, a sulfur atom and an oxygen atom, preferably sulfur or oxygen, preferably a heteroaromatic ring other than pyridyl; a substituted heteroaromatic ring, substituted with up to four substituents selected from a bromine atom, a chlorine atom, a fluorine atom, a trifluoromethyl group, a cyano group, and a nitro gr $R^2$ and $R^3$ are selected from a hydrogen atom, a halogen atom, preferably bromine or chlorine, and a trifluoromethyl group, provided that $R^2$ and $R^3$ are not concurrently halogen;

M is a hydrogen atom; an alkali or alkaline earth metal atom; or a hydrolytically labile group selected from a

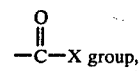

wherein X is a ($C_1$–$C_6$) alkyl group, a ($C_1$–$C_6$) alkoxy group, a ($C_1$–$C_6$) alkylamino group, a ($C_1$–$C_6$) dialkylamino group, or a ($C_1$–$C_6$) alkylthio group; a ($C_1$–$C_6$) alkoxymethyl group; a ($C_1$–$C_6$) alkylthiomethyl group; a halogen atom; a cyano group; and a ($C_1$–$C_6$) alkyl- or ($C_6$–$C_{10}$) aryl-sulfonyl, -sulfinyl, or -sulfenyl group; preferably a sodium atom, a calcium atom, a potassium atom, or a magnesium atom, more preferably a hydrogen atom.

As used in the specification and claims, the term alkyl is meant to include branched as well as straight chain alkyl groups. Representative examples of such groups include methyl, ethyl, propyl, isopropyl, sec-butyl, isobutyl, tert-butyl, pentyl, neopentyl, hexyl, and the like.

By an unsubstituted ($C_6$–$C_{10}$) aryl group is meant an aryl group such as phenyl or naphthyl.

By a substituted ($C_6$–$C_{10}$) aryl group is meant an aryl group such as phenyl or naphthyl, substituted with one or more, but preferably with one to five of the specified substituents.

By alkali and alkaline earth metals is meant sodium, calcium, potassium, and magnesium.

A preferred embodiment of this invention can be represented by the formula:

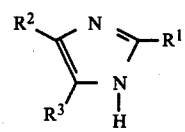

wherein $R^1$ is a trifluoromethyl group, an unsubstituted phenyl group, or a phenyl group substituted with up to 5 substituents selected from a bromine atom, a chlorine atom, a fluorine atom and a trifluoromethyl group; an unsubstituted 2-pyridyl group, a 2-pyridyl group substituted with up to four substituents selected from a bromine atom, a chlorine atom, a fluorine atom, and a trifluoromethyl group; and $R^2$ and $R^3$ are independently a bromine atom or a trifluoromethyl group.

Particularly preferred embodiments of the invention have the following formulae:

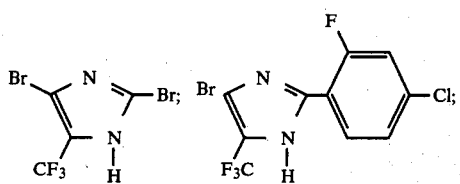

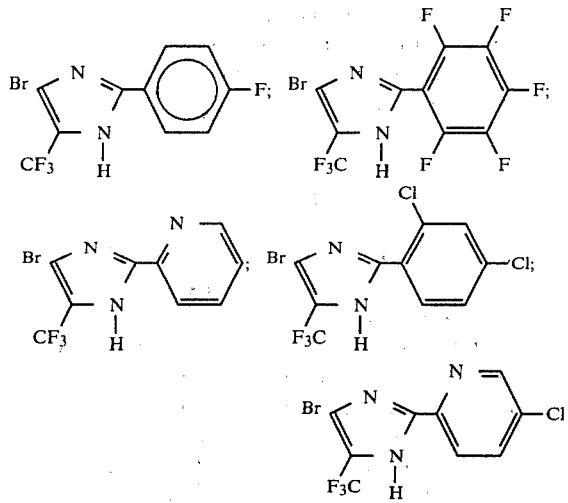

Examples of the compounds of the invention embraced by Formula (I) include:

4-bromo-2-(2-chloro-4-trifluoromethylphenyl)-5-trifluoromethylimidazole
4-bromo-2-(3,5 bistrifluoromethyl phenyl)-5-trifluoromethylimidazole
2,4,5-tristrifluoromethylimidazole
4,5-dibromo-2-(2,4-dichlorophenyl)-imidazole
4,5-dibromo-2-(pentafluorophenyl)-imidazole
4-bromo-5-(4-chloro-2,6-difluorophenyl)-5-trifluoromethylimidazole
4-bromo-2-(4-chloro-2-cyanophenyl)-5-trifluoromethylimidazole
4,5-bistrifluoromethyl-2-(2,4,5-trichlorophenyl) imidazole
4-fluoro-2-(3-cyano-4-fluorophenyl)-5-trifluoromethylimidazole
4-bromo-2-(2-trifluoromethyl-4-bromophenyl)-5-trifluoromethylimidazole
4-bromo-2-(2-bromo-4-methanesulfonylphenyl)-5-trifluoromethylimidazole
4-bromo-2-(2-Methoxy-3-chloro-5-nitrophenyl)-5-trifluoromethylimidazole
4-bromo-2-(3,5dichloropyridyl)-5-trifluoromethylimidazole
4-bromo-2-(2,5dichloro-4-methylthiophenyl)-5-trifluoromethylimidazole
4-Chloro-2-(2-chloro-3-nitrophenyl)-5-trifluoromethylimidazole
Sodium salt of 4-bromo-2-(2-bromo-4-methylsulfonylphenyl)-5-trifluoromethylimidazole
4-bromo-2-(3,5-dichloropyridyl)-1-methoxymethyl-5-trifluoromethylimidazole
4-bromo-2-(2,6 difluoro-4-bromophenyl)-1-methoxycarbonyl-5-trifluoromethylimidazole
4-bromo-2-(2-cyano-5,6-dichlorophenyl)-1-dimethylcarbamoyl-5-trifluoromethylimidazole
4-iodo-2-(2-chloro-4-methanesulfonyl)-5-trifluoromethylimidazole
4-bromo-2-(4-pyrimidyl)-5-trifluoromethylimidazole
4-bromo-2-(5-methanesulfonyl thiadiazolyl)-5-trifluoromethylimidazole
4-bromo-2-[2-(3-fluoro-5-chloro)pyridyl]-5-trifluoromethylimidazole and the pyridine-N-oxide
4-bromo-2-[2-(3-fluoro-5-trifluoromethyl)pyridyl]-5-trifluoromethylimidazole and the pyridine-N-oxide
4-bromo-2-[2-(3-fluoro-5-bromo)pyridyl]-5-trifluoromethylimidazole and the pyridine-N-oxide
4-bromo-2-[2-(3-fluoro-5-trifluoromethoxy)pyridyl]-5-trifluoromethylimidazole and the pyridine-N-oxide
4-bromo-2-[2-(3-fluoro-5-trifluoroacetyl)pyridine]-5-trifluoromethylimidazole and the pyridine-N-oxide
4-bromo-2-[2-(3-fluoro-5-trifluoromethanesulfonyl)pyridyl]5-trifluoromethylimidazole and the pyridine-N-oxide
4-bromo-2-[2-(3-fluoro-5-methanesulfonyl)pyridyl]-5-trifluoromethylimidazole and the pyridine-N-oxide
4-bromo-2-[2-(3-fluoro-5-difluoromethyl)pyridyl]-5-trifluoromethylimidazole and the pyridine-N-oxide
4-bromo-2-[2-(3-fluoro-5-pentafluoroethyl)pyridyl]-5-trifluoromethylimidazole and the pyridine-N-oxide
4-bromo-2-[2-(3-fluoro-5-[1,1-difluoroethyl])pyridyl]-5-trifluoromethylimidazole and the pyridine-N-oxide
4-bromo-2-[2-(3-fluoro-5-carbomethoxy)pyridyl]-5-trifluoromethylimidazole and the pyridine-N-oxide
4-bromo-2-[2-(3,5-difluoro)pyridyl]-5-trifluoromethylimidazole and the pyridine-N-oxide
4-bromo-2-[2-(5-bromo)pyridyl]-5-trifluoromethylimidazole and the pyridine-N-oxide
4-bromo-2-[2-(5-chloro)pyridyl]-5-trifluoromethylimidazole and the pyridine-N-oxide
4-bromo-2-[2-(5-fluoro)pyridyl]-5-trifluoromethylimidazole and the pyridine-N-oxide
4-bromo-2-[2-(5-trifluoromethyl)pyridyl]-5-trifluoromethylimidazole and the pyridine-N-oxide
4-bromo-2-[2-(5-difluoromethyl)pyridyl]-5-trifluoromethylimidazole and the pyridine-N-oxide
4-bromo-2-[2-(5-pentafluoroethyl)pyridyl]-5-trifluoromethylimidazole and the pyridine-N-oxide
4-bromo-2-[2-(5-[1,1-difluoroethyl])pyridyl]-5-trifluoromethylimidazole and the pyridine-N-oxide
4-bromo-2-[2-(5-trifluoromethoxy)pyridyl]-5-trifluoromethylimidazole and the pyridine-N-oxide
4-bromo-2-[2-(5-trifluoroacetyl)pyridyl]-5-trifluoromethylimidazole and the pyridine-N-oxide
4-bromo-2-[2-(5-trifluoromethanesulfonyl)pyridyl]-5-trifluoromethylimidazole and the pyridine-N-oxide
4-bromo-2-[2-(5-methanesulfonyl)pyridyl]-5-trifluoromethylimidazole and the pyridine-N-oxide
4-bromo-2-[2-(5-carbomethoxy)pyridyl]-5-trifluoromethylimidazole and the pyridine-N-oxide
4-bromo-2-[2-(5-bromo)-1,3,4-thiadiazolyl]-5-trifluoromethylimidazole
4-bromo-2-[2-(5-chloro)-1,3,4-thiadiazolyl]-5-trifluoromethylimidazole
4-bromo-2-[2-(5-fluoro)-1,3,4-thiadiazolyl]-5-trifluoromethylimidazole
4-bromo-2-[2-(5-trifluoromethyl)-1,3,4-thiadiazolyl]-5-trifluoromethylimidazole
4-bromo-2-[2-(5-difluoromethyl)-1,3,4-thiadiazolyl]-5-trifluoromethylimidazole
4-bromo-2-[2-(5-pentafluoroethyl)-1,3,4-thiadiazolyl]-5-trifluoromethylimidazole
4-bromo-2-[2-(5-[1,1-difluoroethyl])-1,3,4-thiadiazolyl]-5-trifluoromethylimidazole
4-bromo-2-[2-(5-trifluoromethoxy)-1,3,4-thiadiazolyl]-5-trifluoromethylimidazole
4-bromo-2-[2-(5-trifluoroacetyl)-1,3,4-thiadiazolyl]-5-trifluoromethylimidazole 4-bromo-2-[2-(5-trifluoromethanesulfonyl)-1,3,4-thiadiazolyl]-5-trifluoromethylimidazole
4-bromo-2-[2-(5-methanesulfonyl)-1,3,4-thiadiazolyl]-5-trifluoromethylimidazole
4-bromo-2-[2-(5-carbomethoxy)-1,3,4-thiadiazolyl]-5-trifluoromethylimidazole
4-bromo-2-[2-(5-bromo)pyrimidyl]-5-trifluoromethylimidazole
4-bromo-2-[2-(5-chloro)pyrimidyl]-5-trifluoromethylimidazole
4-bromo-2-[2-(5-fluoro)pyrimidyl]-5-trifluoromethylimidazole
4-bromo-2-[2-(5-trifluoromethyl)pyrimidyl]-5-trifluoromethylimidazole
4-bromo-2-[2-(5-difluoromethyl)pyrimidyl[-5-trifluoromethylimidazole
4-bromo-2-[2-(5-pentafluoroethyl)pyrimidyl]-5-trifluoromethylimidazole
4-bromo-2-[2-(5-[1,1-difluoroethyl)pyrimidyl]-5-trifluoromethylimidazole
4-bromo-2-[2-(5-trifluoromethoxy)pyrimidyl]-5-trifluoromethylimidazole
4-bromo-2-[2-(5-trifluoroacetyl)pyrimidyl]-5-trifluoromethylimidazole
4-bromo-2-[2-(5-trifluoromethanesulfonyl)-pyrimidyl]-5-trifluoromethylimidazole
4-bromo-2-[2-(5-methanesulfonyl)pyrimidyl]-5-trifluoromethylimidazole
4-bromo-2-[2-(5-carbomethoxy)pyrimidyl]-5-trifluoromethylimidazole
4-bromo-2-[3-(6-bromo)-1,2,4-triazinyl]-5-trifluoromethylimidazole
4-bromo-2-[3-(6-chloro)-1,2,4-triazinyl]-5-trifluoromethylimidazole
4-bromo-2-[3-(6-fluoro)-1,2,4-triazinyl]-5-trifluoromethylimidazole
4-bromo-2-[3-(6-trifluoromethyl)-1,2,4-triazinyl]-5-trifluoromethylimidazole
4-bromo-2-[3-(6-difluoromethyl)-1,2,4-triazinyl]-5-trifluoromethylimidazole
4-bromo-2-[3-(6-pentafluoroethyl)-1,2,4-triazinyl]-5-trifluoromethylimidazole
4-bromo-2-[3-(6-[1,1-difluoroethyl])-1,2,4-triazinyl]-5-trifluoromethylimidazole
4-bromo-2-[3-(6-trifluoromethoxy)-1,2,4-triazinyl]-5-trifluoromethylimidazole
4-bromo-2-[3-(6-trifluoroacetyl)-1,2,4-triazinyl]-5-trifluoromethylimidazole
4-bromo-2-[3-(6-trifluoromethanesulfonyl)-1,2,4-triazinyl]-5-trifluoromethylimidazole
4-bromo-2-[3-(6-methanesulfonyl)-1,2,4-triazinyl]-5-trifluoromethylimidazole
4-bromo-2-[3-(6-carbomethyl)-1,2,4-triazinyl]-5-trifluoromethylimidazole
4-bromo-2-[4-(N-methyl)pyridinium]-5-trifluoromethylimidazole chloride, bromide, iodide, tetrafluoroborate
4-bromo-2-[2-(5-bromo)thiazolyl]-5-trifluoromethylimidazole
4-bromo-2-[2-(5-chloro)thiazolyl]-5-trifluoromethylimidazole
4-bromo-2-[2-(5-fluoro)thiazolyl]-5-trifluoromethylimidazole
4-bromo-2-[2-(5-trifluoromethyl)thiazolyl]-5-trifluoromethylimidazole
4-bromo-2-[2-(5-difluoromethyl)thiazolyl]-5-trifluoromethylimidazole
4-bromo-2-[2-(5-pentafluoroethyl)thiazolyl]-5-trifluoromethylimidazole
4-bromo-2-[2-(5-[1,1-difluoroethyl])thiazolyl]-5-trifluoromethylimidazole
4-bromo-2-[2-(5-trifluoromethoxy)thiazolyl]-5-trifluoromethylimidazole
4-bromo-2-[2-(5-trifluoroacetyl)thiazolyl]-5-trifluoromethylimidazole
4-bromo-2-[2-(5-trifluoromethanesulfonyl)thiazolyl]-5-trifluoromethylimidazole
4-bromo-2-[2-(5-methanesulfonyl)thiazolyl]-5-trifluoromethylimidazole
4-bromo-2-[2-(5-carbomethoxy)thiazolyl]-5-trifluoromethylimidazole
4-bromo-2-(4-bromophenyl)-5-trifluoromethylimidazole
4-bromo-2-(4-trifluoromethoxyphenyl)-5-trifluoromethylimidazole
4-bromo-2-(4-difluoromethylphenyl)-5-trifluoromethylimidazole
4-bromo-2-(4-pentafluoroethylphenyl)-5-trifluoromethylimidazole
4-bromo-2-[4-(1,1-difluoroethyl)phenyl]-5-trifluoromethylimidazole
4-bromo-2-(4-trifluoromethanesulfonylphenyl)-5-trifluoromethylimidazole
4-bromo-2-(4-trifluoroacetylphenyl)-5-trifluoromethylimidazole
4-bromo-2-(4-methanesulfonylphenyl)-5-trifluoromethylimidazole
4-bromo-2-(4-carbomethoxyphenyl)-5-trifluoromethylimidazole
4-bromo-2-(2-fluoro-4-bromophenyl)-5-trifluoromethylimidazole
4-bromo-2-(2-fluoro-4-fluorophenyl)-5-trifluoromethylimidazole
4-bromo-2-(2-fluoro-4-trifluoromethylphenyl)-5-trifluoromethylimidazole
4-bromo-2-(2-fluoro-4-difluoromethylphenyl)-5-trifluoromethylimidazole
4-bromo-2-[2-fluoro-4-(1,1-difluoroethyl)phenyl]-5-trifluoromethylimidazole
4-bromo-2-(2-fluoro-4-pentafluoroethylphenyl)-5-trifluoromethylimidazole
4-bromo-2-(2-fluoro-4-trifluoromethoxyphenyl)-5-trifluoromethylimidazole
4-bromo-2-(2-fluoro-4-trifluoroacetylphenyl)-5-trifluoromethylimidazole
4-bromo-2-(2-fluoro-4-trifluoromethanesulfonylphenyl)-5-trifluoromethylimidazole
4-bromo-2-(2-fluoro-4-methanesulfonylphenyl)-5-trifluoromethylimidazole
4-bromo-2-(2-fluoro-4-carbomethoxyphenyl)-5-trifluoromethylimidazole
4-bromo-2-(2-fluoro-4-bromophenyl)-5-trifluoromethylimidazole
4-bromo-2-(2-chloro-4-bromophenyl)-5-trifluoromethylimidazole
4-bromo-2-(2-chloro-4-trifluoromethylphenyl)-5-trifluoromethylimidazole
4-bromo-2-(2-chloro-4-difluoromethylphenyl)-5-trifluoromethylimidazole
4-bromo-2-(2-chloro-4-pentafluoromethylphenyl)-5-trifluoromethylimidazole
4-bromo-2-[2-chloro-4-(1,1-difluoroethyl)phenyl]-5-trifluoromethylimidazole
4-bromo-2-(2-chloro-4-trifluoromethoxyphenyl)-5-trifluoromethylimidazole 4-bromo-2-(2-chloro-4-trifluoroacetylphenyl)-5-trifluoromethylimidazole
4-bromo-2-(2-chloro-4-trifluoromethanesulfonylphenyl)-5-trifluoromethylimidazole
4-bromo-2-(2-chloro-4-methanesulfonylphenyl)-5-trifluoromethylimidazole
4-bromo-2-(2-chloro-4-carbomethoxyphenyl)-5-trifluoromethylimidazole
4-bromo-2-(2-trifluoromethyl-4-bromophenyl)-5-trifluoromethylimidazole
4-bromo-1-(2-trifluoromethyl-4-bromophenyl)-5-trifluoromethylimidazole
4-bromo-2-(2,4-ditrifluoromethylphenyl)-5-trifluoromethylimidazole
4-bromo-2-(2-trifluoromethyl-4-difluoromethylphenyl)-5-trifluoromethylimidazole
4-bromo-2-(2-trifluoromethyl-4-pentafluoroethylphenyl)-5-trifluoromethylimidazole
4-bromo-2-[2-trifluoromethyl-4-pentafluoroethylphenyl)-5-trifluoromethylimidazole
4-bromo-2-(2-trifluoromethyl-4-trifluoromethoxyphenyl)-5-trifluoromethylimidazole
4-bromo-2-(2-trifluoromethyl-4-trifluoroacetylphenyl)-5-trifluoromethylimidazole
4-bromo-2-(2-trifluoromethyl-4-trifluoromethanesulfonylphenyl)-5-trifluoromethylimidazole
4-bromo-2-(2-trifluoromethyl-4-methanesulfonylphenyl)-5-trifluoromethylimidazole
4-bromo-2-(2-trifluoromethyl-4-carbomethoxyphenyl)-5-trifluoromethylimidazole
4-bromo-2-(2-bromo-4-chlorophenyl)-5-trifluoromethylimidazole
4-bromo-2-(2,4-dibromophenyl)-5-trifluoromethylimidazole
4-bromo-2-(2-bromo-4-fluorophenyl)-5-trifluoromethylimidazole
4-bromo-2-(2-bromo-4-trifluorophenyl)-5-trifluoromethylimidazole
4-bromo-2-(2-bromo-4-difluoromethylphenyl)-5-trifluoromethylimidazole
4-bromo-2-(2-bromo-4-pentafluoroethylphenyl)-5-trifluoromethylimidazole
4-bromo-2-[2-bromo-4-(1,1-difluoroethyl)phenyl]-5-trifluoromethylimidazole
4-bromo-2-(2-bromo-4-trifluoromethoxyphenyl)-5-trifluoromethylimidazole
4-bromo-2-(2-bromo-4-trifluoroacetylphenyl)-5-trifluoromethylimidazole
4-bromo-2-(2-bromo-4-trifluoromethanesulfonylphenyl)-5-trifluoromethylimidazole
4-bromo-2-(2-bromo-4-carbomethoxyphenyl)-5-trifluoromethylimidazole
4-bromo-2-(2-bromo-4-chloro-5-ethoxyphenyl)-5-trifluoromethylimidazole
4-bromo-2-(2-bromo-4-chloro-5-isopropoxyphenyl)-5-trifluoromethylimidazole
4-bromo-2-(2-bromo-4-chloro-5-carbomethoxyphenyl)-5-trifluoromethylimidazole
4-bromo-2-(2-bromo-4-chloro-5-carboisopropoxyphenyl)-5-trifluoromethylimidazole
4-bromo-2-(2,4-difluoro-5-ethoxyphenyl)-5-trifluoromethylimidazole
4-bromo-2-(2,4-difluoro-5-isopropoxyphenyl)-5-trifluoromethylimidazole
4-bromo-2-(2,4-difluoro-5-carbomethoxyphenyl)-5-trifluoromethylimidazole
4-bromo-2-(2,4-difluoro-5-carboisopropoxyphenyl)-5-trifluoromethylimidazole
4-bromo-2-(2-fluoro-4-trifluoromethyl-5-ethoxyphenyl)-5-trifluoromethylimidazole
4-bromo-2-(2-fluoro-4-trifluoromethyl-5-isopropoxyphenyl)-5-trifluoromethylimidazole
4-bromo-2-(2-fluoro-4-trifluoromethyl-5-carbomethoxyphenyl)-5-trifluoromethylimidazole
4-bromo-2-(2-fluoro-4-trifluoromethyl-5-carboisopropoxyphenyl)-5-trifluoromethylimidazole
4-bromo-2-(2-fluoro-4-bromo-5-ethoxyphenyl)-5-trifluoromethylimidazole
4-bromo-2-(2-fluoro-4-bromo-5-isopropoxyphenyl)-5-trifluoromethylimidazole
4-bromo-2-(2-fluoro-4-bromo-5-carbomethoxyphenyl)-5-trifluoromethylimidazole
4-bromo-2-(2-fluoro-4-bromo-5-carboisopropoxyphenyl)-5-trifluoromethylimidazole
4-bromo-2-(2-fluoro-4-difluoromethyl-5-ethoxyphenyl)-5-trifluoromethylimidazole
4-bromo-2-(2-fluoro-4-difluoromethyl-5-isopropoxyphenyl)-5-trifluoromethylimidazole
4-bromo-2-(2-fluoro-4-difluoromethyl-5-carbomethoxyphenyl)-5-trifluoromethylimidazole
4-bromo-2-(2-fluoro-4-difluoromethyl-5-carboisopropoxyphenyl)-5-trifluoromethylimidazole
4-bromo-2-(2-fluoro-4-pentafluoroethyl-5-ethoxyphenyl)-5-trifluoromethylimidazole
4-bromo-2-(2-fluoro-4-pentafluoroethyl-5-isopropoxyphenyl)-5-trifluoromethylimidazole
4-bromo-2-(2-fluoro-4-pentafluoroethyl-5-carbomethoxyphenyl)-5-trifluoromethylimidazole
4-bromo-2-(2-fluoro-4-pentafluoroethyl-5-carboisopropoxyphenyl)-5-trifluoromethylimidazole
4-bromo-2-[2-fluoro-4-(1,1-difluoroethyl)-5-ethoxyphenyl]-5-trifluoromethylimidazole
4-bromo-2-[2-fluoro-4-(1,1-difluoroethyl)-5-isopropoxyphenyl]-5-trifluoromethylimidazole
4-bromo-2-[2-fluoro-4-(1,1-difluoroethyl)-5-carbomethoxyphenyl]-5-trifluoromethylimidazole
4-bromo-2-[2-fluoro-4-(1,1-difluoroethyl)-5-carboisopropoxyphenyl]-5-trifluoromethylimidazole
4-bromo-2-(2-fluoro-4-trifluoromethoxy-5-ethoxyphenyl)-5-trifluoromethylimidazole
4-bromo-2-(2-fluoro-4-trifluoromethoxy-5-isopropoxyphenyl)-5-trifluoromethylimidazole
4-bromo-2-(2-fluoro-4-trifluoromethoxy-5-carbomethylphenyl)-5-trifluoromethylimidazole
4-bromo-2-(2-fluoro-4-trifluoromethoxy-5-carboisopropoxyphenyl)-5-trifluoromethylimidazole
4-bromo-2-(2-fluoro-4-trifluoroacetyl-5-ethoxyphenyl)-5-trifluoromethylimidazole
4-bromo-2-(2-fluoro-4-trifluoroacetyl-5-isopropoxyphenyl)-5-trifluoromethylimidazole
4-bromo-2-(2-fluoro-4-trifluoroacetyl-5-carbomethoxyphenyl)-5-trifluoromethylimidazole
4-bromo-2-(2-fluoro-4-trifluoroacetyl-5-carboisopropoxyphenyl)-5-trifluoromethylimidazole
4-bromo-2-(2-fluoro-4-trifluoromethanesulfonyl-5-ethoxyphenyl)-5-trifluoromethylimidazole
4-bromo-2-(2-fluoro-4-trifluoromethanesulfonyl-5-isopropoxyphenyl)-5-trifluoromethylimidazole
4-bromo-2-(2-fluoro-4-trifluoromethanesulfonyl-5-carbomethoxyphenyl)-5-trifluoromethylimidazole
4-bromo-2-(2-fluoro-4-trifluoromethanesulfonyl-5-carboisopropoxyphenyl)-5-trifluoromethylimidazole
4-bromo-2-(2-fluoro-4-methanesulfonyl-5-ethoxyphenyl)-5-trifluoromethylimidazole 4-bromo-2-(2-fluoro-4-methanesulfonyl-5-isopropoxyphenyl)-5-trifluoromethylimidazole
4-bromo-2-(2-fluoro-4-methaneslfonyl-5-carbomethoxyphenyl)-5-trifluoromethylimidazole
4-bromo-2-(2-fluoro-4-methanesulfonyl-5-carboisopropoxyphenyl)-5-trifluoromethylimidazole
4-bromo-2-(2-fluoro-4-carbomethoxy-5-ethoxyphenyl)-5-trifluoromethylimidazole
4-bromo-2-(2-fluoro-4-carbomethoxy-5-isopropoxyphenyl)-5-trifluoromethylimidazole
4-bromo-2-(2-fluoro-4-carbomethoxy-5-carbomethoxyphenyl)-5-trifluoromethylimidazole
4-bromo-2-(2-fluoro-4-carbomethoxy-5-carboisopropoxyphenyl)-5-trifluoromethylimidazole
4-bromo-2-(2,6-difluoro-4-bromophenyl)-5-trifluoromethylimidazole
4-bromo-2-(2,6-difluoro-4-chlorophenyl)-5-trifluoromethylimidazole
4-bromo-2-(2,4,6-trifluorophenyl)-5-trifluoromethylimidazole
4-bromo-2-(2,6-difluoro-4-trifluoromethylphenyl)-5-trifluoromethylimidazole
4-bromo-2-(2,6-difluoro-4-difluoromethylphenyl)-5-trifluoromethylimidazole
4-bromo-2-(2,6-difluoro-4-pentafluoroethylphenyl)-5-trifluoromethylimidazole
4-bromo-2-[2,6-difluoro-4-(1,1-difluoroethyl)phenyl]-5-trifluoromethylimidazole
4-bromo-2-(2,6-difluoro-4-trifluoromethoxyphenyl)-5-trifluoromethylimidazole
4-bromo-2-(2,6-difluoro-4-trifluoroacetylphenyl)-5-trifluoromethylimidazole
4-bromo-2-(2,6-difluoro-4-trifluoromethanesulfonylphenyl)-5-trifluoromethylimidazole
4-bromo-2-(2,6-difluoro-4-methanesulfonylphenyl)-5-trifluoromethylimidazole
4-bromo-2-(2,6-difluoro-4-carbomethoxyphenyl)-5-trifluoromethylimidazole
4-bromo-2-(2-fluoro-4-bromo-6-chlorophenyl)-5-trifluoromethylimidazole
4-bromo-2-(2-fluoro-4,6-dichlorophenyl)-5-trifluoromethylimidazole
4-bromo-2-(2-fluoro-4-trifluoromethyl-6-chlorophenyl)-5-trifluoromethylimidazole
4-bromo-2-(2,4-difluoro-6-chlorophenyl)-5-trifluoromethylimidazole
4-bromo-2-(2-fluoro-4-difluoromethyl-6-chlorophenyl)-5-trifluoromethylimidazole
4-bromo-2-(2-fluoro-4-pentafluoroethyl-6-chlorophenyl)-5-trifluoromethylimidazole
4-bromo-2-[2-fluoro-4-(1,1-difluoroethyl)-6-chlorophenyl]-5-trifluoromethylimidazole
4-bromo-2-(2-fluoro-4-trifluoromethoxy-6-chlorophenyl)-5-trifluoromethylimidazole
4-bromo-2-(2-fluoro-4-trifluoroacetyl-6-chlorophenyl)-5-trifluoromethylimidazole
4-bromo-2-(2-fluoro-4-methanesulfonyl-6-chlorophenyl)-5-trifluoromethylimidazole
4-bromo-2-(2-fluoro-4-carbomethoxy-6-chlorophenyl)-5-trifluoromethylimidazole
4-bromo-2-(2-fluoro-4,6-dibromophenyl)-5-trifluoromethylimidazole
4-bromo-2-(2-fluoro-4-chloro-6-bromophenyl)-5-trifluoromethylimidazole
4-bromo-2-(2-fluoro-4-trifluoromethyl-6-bromophenyl)-5-trifluoromethylimidazole
4-bromo-2-(2,4-difluoro-6-bromophenyl)-5-trifluoromethylimidazole
4-bromo-2-(2-fluoro-4-difluoromethyl-6-bromophenyl)-5-trifluoromethylimidazole
4-bromo-2-[2-fluoro-4-pentafluoroethyl-6-bromophenyl)-5-trifluoromethylimidazole
4-bromo-2-[2-fluoro-4-(1,1-difluoroethyl)-6-bromophenyl]-5-trifluoromethylimidazole
4-bromo-2-(2-fluoro-4-trifluoromethoxy-6-bromophenyl)-5-trifluoromethylimidazole
4-bromo-2-(2-fluoro-4-trifluoroacetyl-6-bromophenyl)-5-trifluoromethylimidazole
4-bromo-2-(2-fluoro-4-trifluoromethanesulfonyl-6-bromophenyl)-5-trifluoromethylimidazole
4-bromo-2-(2-fluoro-4-methanesulfonyl-6-bromophenyl)-5-trifluoromethylimidazole
4-bromo-2-(2-fluoro-4-carbomethoxy-6-bromophenyl)-5-trifluoromethylimidazole
4-bromo-2-(2,4,6-trichlorophenyl)-5-trifluoromethylimidazole
4-bromo-2-(2-fluoro-6-bromophenyl)-5-trifluoromethylimidazole
4-bromo-2-(2-fluoro-6-chlorophenyl)-5-trifluoromethylimidazole
4-bromo-2-(2,6-difluorophenyl)-5-trifluoromethylimidazole
4-bromo-2-(2-fluoro-6-trifluoromethylphenyl)-5-trifluoromethylimidazole
4-bromo-2-(2-fluoro-6-difluoromethylphenyl)-5-trifluoromethylimidazole
4-bromo-2-(2-fluoro-6-pentafluoromethylphenyl)-5-trifluoromethylimidazole
4-bromo-2-[2-fluoro-6-(1,1-difluoroethyl)phenyl]-5-trifluoromethylimidazole
4-bromo-2-(2-fluoro-6-trifluoromethoxyphenyl)-5-trifluoromethylimidazole
4-bromo-2-(2-fluoro-6-trifluoroacetylphenyl)-5-trifluoromethylimidazole
4-bromo-2-(2-fluoro-6-methanesulfonylphenyl)-5-trifluoromethylimidazole
4-bromo-2-(2-fluoro-6-carbomethoxyphenyl)-5-trifluoromethylimidazole
4-bromo-2-[3-(6-bromo)pyridazinyl]-5-trifluoromethylimidazole
4-bromo-2-[3-(6-chloro)pyridazinyl]-5-trifluoromethylimidazole
4-bromo-2-[3-(6-fluoro)pyridazinyl]-5-trifluoromethylimidazole
4-bromo-2-[3-(6-trifluoromethyl)pyridazinyl]-5-trifluoromethylimidazole
4-bromo-2-[3-(6-difluoromethyl)pyridazinyl]-5-trifluoromethylimidazole
4-bromo-2-[3-(6-pentafluoroethyl)pyridazinyl]-5-trifluoromethylimidazole
4-bromo-2-[3-(6-[1,1-difluoroethyl])pyridazinyl]-5-trifluoromethylimidazole
4-bromo-2-[3-(6-trifluoromethoxy)pyridazinyl]-5-trifluoromethylimidazole
4-bromo-2-[3-(6-trifluoroacetyl)pyridazinyl]-5-trifluoromethylimidazole
4-bromo-2-[3-(6-methanesulfonyl)pyridazinyl]-5-trifluoromethylimidazole
4-bromo-2-[3-(6-carbomethoxy)pyridazinyl]-5-trifluoromethylimidazole
4-bromo-2-[3-(4-fluoro-6-bromo)pyridazinyl]-5-trifluoromethylimidazole
4-bromo-2-[3-(4-fluoro-6-chloro)pyridazinyl]-5-trifluoromethylimidazole
4-bromo-2-[3-(4,6-difluoro)pyridazinyl]-5-trifluoromethylimidazole 4-bromo-2-[3-(4-fluoro-6-trifluoromethyl)-pyridazinyl]-5-trifluoromethylimidazole
4-bromo-2-[3-(4-fluoro-6-difluoromethyl)-pyridazinyl]-5-trifluoromethylimidazole
4-bromo-2-[3-(4-fluoro-6-pentafluoroethyl)-pyridazinyl]-5-trifluoromethylimidazole
4-bromo-2-[3-(4-fluoro-[1,1-difluoroethyl]-)pyridazinyl]-5-trifluoromethylimidazole
4-bromo-2-[3-(4-fluoro-6-trifluoromethoxy)-pyridazinyl]-5-trifluoromethylimidazole
4-bromo-2-[3-(4-fluoro-6-trifluoroacetyl)-pyridazinyl]-5-trifluoromethylimidazole
4-bromo-2-[3-(4-fluoro-6-trifluoromethanesulfonyl)-pyridazinyl]-5-trifluoromethylimidazole
4-bromo-2-[3-(4-fluoro-6-methanesulfonyl)-pyridazinyl]-5-trifluoromethylimidazole
4-bromo-2-[3-(4-fluoro-6-carbomethoxy)-pyridazinyl]-5-trifluoromethylimidazole These compounds can be summarized by the following structures:

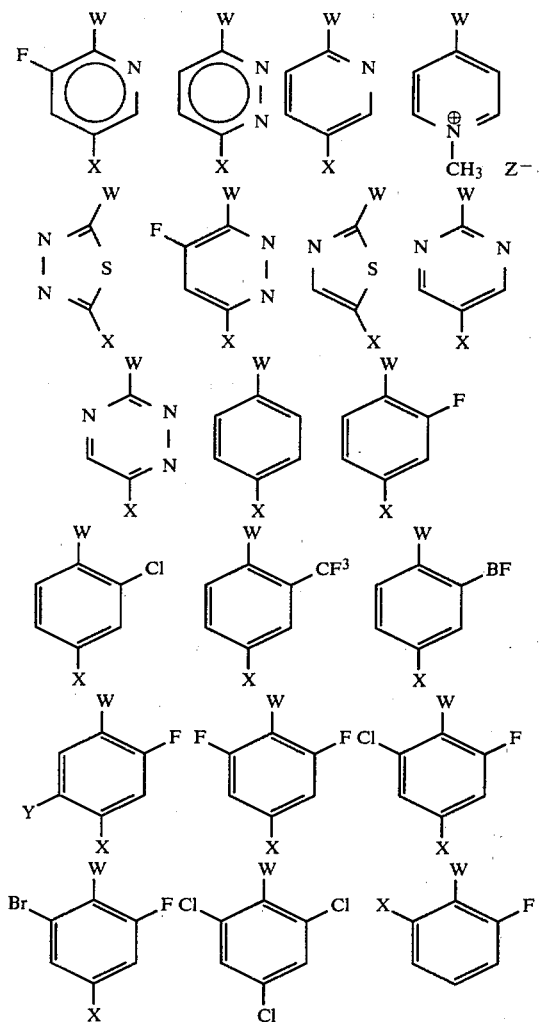

wherein
X=Br, Cl, $CF_3$, $CHF_2$, $C_2F_5$, $CH_3CF_2$, $CF_3O$, $CF_3CO$, $CF_3SO_2$, $CH_3SO_2$, or $CO_2CH_3$;
Y=$OC_2H_5$, O—i—$C_3H_7$, $CO_2CH_3$, or $CO_2$—i—$C_3H_7$;
Z=$Cl^\ominus$, $Br^\ominus$, $I^\ominus$ or $BF_4^\ominus$; and

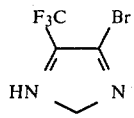

The novel substituted imidazoles of the invention are useful both as preemergence and as postemergence herbicides. Preemergence herbicides are ordinarily used to treat the soil in which the desired crop is to be planted by application either before seeding, during seeding, or, as in most applications, after seeding and before the crop emerges. Postemergence herbicides are those which are applied after the plants have emerged and during their growth period. Non-selective post emergence herbicides are used for ground preparation in no-till agriculture, in total weed control, as in orchards, rights-of-way, etc. or as post directed sprays.

The substituted imidazoles of the invention can be applied in any amount which will give the required control of weeds. A preferred rate of application of the herbicides of the invention is from about 0.1 to about 12 pounds of the substituted imidazoles per acre.

A substituted imidazole of the invention can be applied to the growth medium or to plants to be treated either by itself or, as is generally done, as a component in a herbicidal composition or formulation which also comprises an agronomically acceptable carrier. By agronomically acceptable carrier is meant any substance which can be used to dissolve, disperse, or diffuse a herbicidal compound in the composition without impairing the effectiveness of the herbicidal compound and which by itself has no detrimental effect on the soil, equipment, crops, or agronomic environment. Mixtures of the substituted imidazoles of the invention may also be used in any of these herbicidal formulations. The herbicidal compositions of the invention can be either solid or liquid formulations or solutions. For example, the substituted imidazoles can be formulated as liquid concentrate, wettable powders, emulsifiable concentrates, dusts, granular formulations, aerosols, or flowable emulsion concentrates. In such formulations, the compounds are extended with a liquid or a solid carrier and, when desired, suitable surfactants are incorporated.

It is usually desirable, particularly in postemergence applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers 1969 Annual."

The substituted imidazole compounds of this invention can be dissolved in any appropriate solvent. Examples of solvents which are useful in the practice of this invention include water, alcohols, ketones, dimethylformamide, dioxane, dimethyl sulfoxide, and the like. Mixtures of these solvents can also be used. The concentration of the solution can vary from about 2% to about 98% with a preferred range being about 25% to about 75%.

For the preparation of emulsifiable concentrates, the substituted imidazoles can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifiers include, for example, the ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates is usually about 10% to 60% and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to 98%, preferably about 40% to 75%. A dispersing agent can constitute about 0.5% to about 3% of the composition, and a wetting agent can constitute from about 0.1% to about 5% of the composition.

Dusts can be prepared by mixing the compounds of the invention with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing about 20% to 80% of the active ingredient are commonly made and are subsequently diluted to about 1% to 10% use concentration.

Granular formulations can be prepared by impregnating a solid such as granular fuller's earth, vermiculite, ground corn cobs, seed hulls, including bran or other grain-hulls, substituted imidazoles in a volatile organic solvent can be sprayed or mixed with the granular solid and the solvent then removed by evaporation. The granular material can have any suitable size, with a preferable size range of 16 to 60 mesh. The substituted imidazoles will usually comprise about 2 to 15% of the granular formulation.

The substituted imidazoles of the invention can also be mixed with fertilizers or fertilizing materials before their application. In one type of solid fertilizing composition in which the substituted imidazoles can be used, particles of a fertilizer or fertilizing ingredients, such as ammonium sulfate, ammonium nitrate, or ammonium phosphate, can be coated with one or more of the substituted imidazoles. The solid substituted imidazoles and solid fertilizing material can also be admixed in mixing or blending equipment, or they can be incorporated with fertilizers in granular formulations. Any relative proportion of substituted imidazoles and fertilizer can be used which is suitable for the crops and weeds to be treated. The substituted imidazoles will commonly be from about 5% to about 25% of the fertilizing composition. These compositions provide fertilizing materials which promote the rapid growth of desired plants, and at the same time control the growth of undesired plants.

The substituted imidazoles of the invention can be applied as herbicidal sprays by methods commonly employed, such as conventional high-gallonage hydraulic sprays, low-gallonage sprays, airblast spray, aerial sprays and dusts. For low volume applications a solution of the compound is usually used. The dilution and rate of application will usually depend upon such factors as the type of equipment employed, the method of application, the area to be treated and the type and stage of development of the weeds.

For some applications, it may be desirable to add one or more other herbicides along with substituted imidazoles of the invention. Examples of other herbicides which can be incorporated to provide additional advantages and effectiveness include:

Carboxylic Acids and Derivatives 2,3,6-trichlorobenzoic acid and its salts
2,3,5,6-tetrachlorobenzoic acid and its salts
2-methoxy-3,5,6-trichlorobenzoic acid and its salts
2-methoxy-3,6-dichlorobenzoic acid and its salts
2-methyl-3,6-dichlorobenzoic acid and its salts
2,3-dichloro-6-methylbenzoic acid and its salts
2,4-dichlorophenoxyacetic acid and its salts and esters
2,4,5-trichlorophenoxyacetic acid and its salts and esters
2-methyl-4-chlorophenoxyacetic acid and its salts and esters
2-(2,4,5-trichlorophenoxy)propionic acid and its salts and esters
4-(2,4-dichlorophenoxy)butyric acid and its salts and esters
4-(2-methyl-4-chlorophenoxy)butyric acid and its salts and esters
2,3,6-trichlorophenylacetic acid and its salts
3,6-endoxohexahydrophthalic acid
dimethyl 2,3,5,6-tetrachloroterephthalate trichloracetic acid and its salts
2,2-dichloropropionic acid and its salts
2,3-dichloroisobutyric acid and its salts Carbamic Acid Derivatives ethyl N,N-di(n-propyl)thiolcarbamate
propyl N,N-di(n-propyl)thiolcarbamate
ethyl N-ethyl-N-(n-butyl)thiolcarbamate
propyl N-ethyl-N-(n-butyl)thiolcarbamate-2-chlorallyl
N,N-diethyldithiocarbamate
N-methyldithiocarbamic acid salts
ethyl 1-hexamethyleneiminecarbothiolate
isopropyl N-phenylcarbamate
isopropyl N-(m-chlorophenyl)carbamate4-chloro-2-butynyl
N-(m-chlorophenyl)carbamate
methyl N-(3,4-dichlorophenyl)carbamate Phenols dinitro-o-(sec-butyl)phenol and its salts
pentachlorophenol and its salts Substituted Ureas 3-(3,4-dichlorophenyl)-1,1-dimethylurea
3-phenyl-1,1-dimethylurea
3-(3,4-dichlorophenyl)-3-methoxy-1,1-dimethylurea
3-(4-chlorophenyl)-3-methoxy-1,1-dimethylurea3-(3,4-dichlorophenyl)-1-n-butyl-1-methylurea
3-(3,4-dichlorophenyl)-1-methoxy-1-methylurea 3-(4-dichlorophenyl)-1-methoxy-1-methylurea
3-(3,4-dichlorophenyl)-1,1,3-trimethylurea
3-(3,4-dichlorophenyl)-1,1-diethylurea dichloral urea

Substituted Triazines 2-chloro-4,6-bis(ethylamino)-s-triazine
2-chloro-4-ethylamino-6-isopropylamino-s-triazine
2-chloro-4,6-bis(methoxypropylamino)-s-triazine
2-methoxy-4,6-bis(isopropylamino)-s-triazine
2-chloro-4-ethylamino-6-(3-methoxypropylamino)-s-triazine
2-methylmercapto-4,6-bis(isopropylamino)-s-triazine
2-methylmercapto-4,6-bis(ethylamino)-s-triazine
2-methylmercapto-4-ethylamino-6-isopropylamino-s-triazine-
2-chloro-4,6-bis(isopropylamino)-s-triazine
2-methoxy-4,6-bis(ethylamino)-s-triazine
2-methoxy-4-ethylamino-6-isopropylamino-s-triazine
2-methylmercapto-4-(2-methoxyethylamino)-6-isopropylamino-s-triazine

Diphenyl Ether Derivatives 2,4-dichloro-4'-nitrodiphenyl ether
2,4,6-trichloro-4'-nitrodiphenyl ether
2,4-dichloro-6-fluoro-4'-nitrodiphenyl ether
3-methyl-4'-nitrodiphenyl ether
3,5-dimethyl-4'-nitrodiphenyl ether
2,4-dinitro-4-trifluoromethyldiphenyl ether
2,4-dichloro-3'-methoxy-4'-nitrodiphenyl ether
2-chloro-3'-ethoxy-4'-nitro-4-trifluoromethyl diphenylether
Sodium 5-(2-chloro-4-trifluoromethyl phenoxy)-2-nitro benzoate

Anilides

N-(3,4-dichlorophenyl)propionamide
N-(3,4-dichlorophenyl)methacrylamideN-(3-chloro-4-methylphenyl)-2-methylpentanamide
N-(3,4-dichlorophenyl)trimethylacetamide
N-(3,4-dichlorophenyl-α,α-dimethylvaleramide
N-isopropyl-N-phenylchloroacetamide
N-n-butoxymethyl-N-(2,6-diethylphenyl)-chloroacetamide
N-n-methoxymethyl-N-(2,6-diethylphenyl)-chloroacetamide

Uracils 5-bromo-3-s-butyl-6-methyluracil
5-bromo-3-cyclohexyl-1,6-dimethyluracil
3-cyclohexyl-5,6-trimethyleneuracil
5-bromo-3-isopropyl-6-methyluracil 3-tert-butyl-5-chloro-6-methyluracil

Nitriles 2,6-dichlorobenzonitrile diphenylacetonitrile
3,5-dibromo-4-hydroxybenzonitrile
3,5-diiodo-4-hydroxybenzonitrile

Other Organic Herbicides 2-chloro-N,N-diallylacetamide
N-(1,1-dimethyl-2-propynyl)-3,5-dichlorobenzamide maleic hydrazide
3-amino-1,2,4-triazole
monosodium methanearsonate
disodium methanearsonate
N,N-dimethyl-α,α-diphenylacetamide
N,N-di(n-propyl)-2,6-dinitro-4-trifluoromethylaniline
N,N-di(n-propyl)-2,6-dinitro-4-methylaniline
N,N-di(n-propyl)-2,6-dinitro-4-methylsulfonylaniline
O-(2,4-dichlorophenyl)-O-methyl-isopropylphosphoramidothioate
4-amino-3,5,6-trichloropicolinic acid
2,3-dichloro-1,4-naphthoquinone
1,1' ethylene-2,2'-bipyridinium dibromide
N-phosphonomethyl glycine
di(methoxythiocarbonyl)disulfide
3-isopropyl-1H-2,1,3-benzothiadiazine-(4)3H-one-2,2-dioxide
1,1'-dimethyl-4,4'-bipyridinium salts
3,4,5,6-tetrahydro-3,5-dimethyl-2-thio-2H-1,3,5-thiadiazine When mixtures of herbicides are employed, the relative proportions which are used will depend upon the crop to be treated and the degree of selectivity in weed control which is desired. Typically the ratio by weight of the herbicide of the invention to other herbicide in such mixtures is between 1:50 and 50:1.

The compounds of the present invention can be prepared by a variety of methods. One method involves reacting a α-haloketone with an amidine. The general reaction can be represented by the following equation:

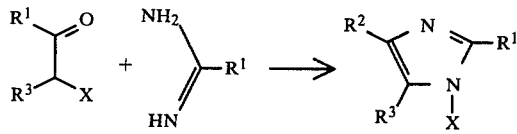

wherein $R^1$, $R^2$, $R^3$ and X are as defined for Formula I.

Another method involves reacting a nitrile with a 1,2 diamine, followed by oxidation. The general reaction can be represented by the following equation:

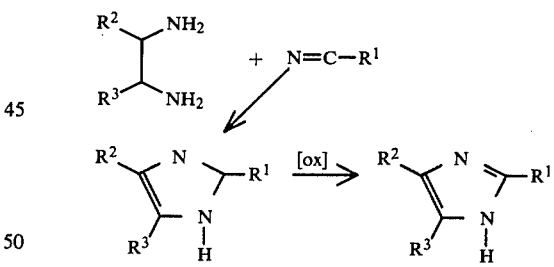

A third method involves the condensation reaction of a glyoxal derivative with an aldehyde and ammonia. The general reaction can be represented by the following equation:

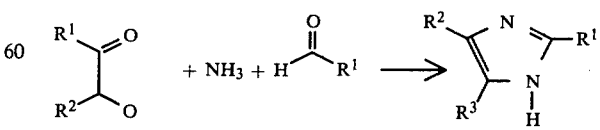

A fourth method involves the condensation reaction of a glyoxal derivative with a substituted 1,1-dibromomethane and ammonia. The general reaction can be represented by the following equation:

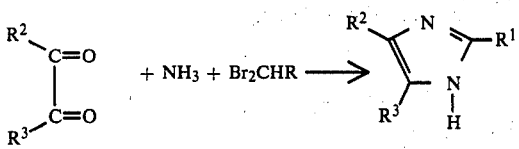

Generally, a stoichiometric ratio of reactants is preferred. While not required, the reaction is advantageously carried out in the presence of an inert organic solvent, polar solvents are preferred. Suitable solvents include, for example, ethyl ether, dioxane, tetrahydrofuran, toluene, chlorobenzene, dimethylsulfoxide, ethanol, water, dimethyl formamide, acetonitrile, and the like. The reaction is generally conducted in a temperature range of about −10° to 100° C. or more, and preferably in the range of about 0° to about 60° C.

All of the starting materials used in the preparation of the compounds of this invention are known compounds or are readily prepared by adaptations of known routes.

The following compounds are given by way of illustration, and are not to be considered as limitations of the present invention.

EXAMPLE 1

2-(3-Chlorophenyl)-5-trifluoromethylimidazole

Sodium acetate 6.6 g (0.08 mol) is dissolved in 20 ml water and 10.8 g (0.04 mol) 3,3-dibromo-1,1,1-trifluoroacetone added. The solution is heated briefly and cooled. Ammonium hydroxide, 40 ml, and 5.6 g (0.04) 3-chlorobenzaldehyde are added. Methanol is added to obtain a homogeneous solution (150 ml). The reaction mixture is stirred for 4 hours. The residual ammonia and the methanol are stripped off in vacuo and the residue extracted with ether. The ether layer is dried over sodium sulfate and filtered through silica gel. The solution is evaporated to yield an oil which solidifies on standing. The solid is recrystallized from chloroform-hexane m.p. 186°–187° C. yield 4.1 g.

EXAMPLE 2

4-Bromo-2-(3-chlorophenyl)-5-trifluoromethylimidazole

Potassium carbonate is made into a paste by adding a few drops of water to 1.3 g (9.4 mol) of the potassium carbonate. The 2-(3-chlorophenyl)-5-trifluoromethylimidazole is dissolved in 100 ml chloroform and added to the flask containing the paste. 1.5 g of bromine is added and stirred. Thin layer chromatography (TLC) on alumina using 50:50 acetone-hexane clearly differentiates starting material from product. Additional bromine is added until starting material is no longer present (0.1 g). Water is added and the organic phase removed. The layer is washed with sodium bisulfite, brine and dried over sodium sulfate. The organic phase is stripped and the residue taken up in 1:1 ether hexane and filtered through silica gel, the filtrate is concentrated to yield 1.7 g product. M.P. 137°–144° C.

EXAMPLE 3

4-Bromo-2-(3,5-dichlorophenyl)-5-trifluoromethylimidazole

Sodium bicarbonate is made into a paste by adding a few drops of water to 1.5 g (9.4 mol). The 2-(3,5-dichlorophenyl)-5-trifluoromethylimidazole is dissolved in 100 ml chloroform and added to the flask containing the paste. 1.5 g of bromine is added and stirred. TLC on alumina using 50:50 acetone-hexane clearly differentiates starting material from product. Additional bromine is added until starting material is no longer present (0.1 g). Water is added and the organic phase removed. The layer is washed with sodium bisulfite, brine and dried over sodium sulfate. The organic phase is stripped and the residue taken up in 1:1 ether hexane and filtered through silica gel.

EXAMPLE 4

Sodium 2,4-dibromo-5-trifluoromethylimidazole 2,4-dibromo-5-trifluoromethylimidazole is dissolved in methanol. A methanol solution containing an equivalent amount of sodium hydroxide is added, stir for 15 minutes and strip to yield product.

EXAMPLE 5

Preparation of 2,5-bistrifluoromethyl-4-bromoimidazole 2,5-bistrifluoromethylimidazole is dissolved in an aqueous solution of potassium carbonate. Bromine 1.1 equivalents is added and heated until color dissipates. Solution is acidified with dilute hydrochloric acid and extracted with ether. The ether layer is washed once with brine solution, dried over sodium sulfate and stripped to give product in 64% yield.

Analogous methods of preparation can be used to prepare the compounds of this invention.

The following examples are given by way of illustration and are not to be considered as limitations of the present invention. In Table I, typical substituted imidazoles of the invention are listed with their melting points and elemental analyses.

EXAMPLE 6

4-Bromo-2-(2,3,4,5,6-pentafluorophenyl)-5-trifluoromethylimidazole

Sodium bicarbonate is made into a paste by adding a few drops of water to 1.5 g (9.4 mol). The 2-(2,3,4,5,6-pentafluorophenyl)-5-trifluoromethylimidazole is dissolved in 100 ml chloroform and added to the flask containing the paste. 1.5 g of bromine is added and stirred. TLC on alumina using 50:50 acetone-hexane clearly differentiates starting material from product. Additional bromine is added until starting material is no longer present (0.1 g). Water is added and the organic phase removed. The layer is washed with sodium bisulfite, brine and dried over sodium sulfate. The organic phase is stripped and the residue taken up in 1:1 ether hexane and filtered through silica gel.

EXAMPLE 7

4-Bromo-2-(2,4-dichlorophenyl)-5-trifluoromethylimidazole

Sodium bicarbonate is made into a paste by adding a few drops of water to 1.5 g (9.4 mol). The 2-(2,4-dichlorophenyl)-5-trifluoromethylimidazole is dissolved in 100 ml chloroform and added to the flask containing the paste. 1.5 g of bromine is added and stirred. TLC on alumina using 50:50 acetone-hexane clearly differentiates starting material from product. Additional bromine is added until starting material is no longer present (0.1 g). Water is added and the organic phase removed. The layer is washed with sodium bisulfite, brine and dried over sodium sulfate. The organic phase is stripped and the residue taken up in 1:1 ether hexane and filtered through silica gel.

EXAMPLE 8

2-[2-(5-chloro)pyridyl]-5-trifluoromethylimidazole

Sodium acetate 6.6 g (0.08 mol) is dissolved in 20 ml water and 10.8 g (0.04 mol) 3,3-dibromo-1,1,1-trifluoroacetone added. The solution is heated briefly then cooled. Ammonium hydroxide, 40 ml, and 5.65 g (0.04 mol) 5-chloro-2-pyridine carboxaldehyde are added. Methanol is added to obtain a homogeneous solution (150 ml). The reaction mixture is stirred overnight. The residual ammonia and the methanol are stripped off in vacuo and the residue extracted with ether. The ether layer is dried over sodium sulfate and filtered through silica gel. The solution is evaporated to yield the product.

EXAMPLE 9

4,5-dibromo-2-(2,3,4,5,6-pentafluorophenyl)-imidazole

To a solution of 10 ml in aqueous sodium hydroxide and 30 ml methanol is added 2.34 g (0.01 ml) 2-(2,3,4,5,6-pentafluorophenyl)imidazole. The solution is heated briefly then cooled. 3.2 g of bromine is added and the reaction stirred. TLC on alumina using 33% acetone/hexanes clearly differentiates starting material from product. If necessary additional bromine is added until starting material is no longer present. Concentrated hydrochloric acid is added until pH 3 is obtained. The reaction mixture is filtered and the crude product collected and dried. The crude product is dissolved in ether and filtered through silica gel. The solvent is removed to yield the product.

EXAMPLE 10

4,5-dibromo-2-(2,4-dichlorophenyl)imidazole

To a solution of 10 ml 1N aqueous sodium hydroxide and 30 ml methanol is added 2.13 g (0.01 mol) 2-(2,4-dichlorophenyl)imidazole. The solution is heated briefly then cooled. 3.2 g of bromine is added and the reaction stirred. TLC on alumina using 33% acetone/hexanes clearly differentiates starting material from product. If necessary additional bromine is added until starting material is no longer present. Concentrated hydrochloric acid is added until pH 3 is obtained. The reaction mixture is filtered and the crude product collected and dried. The crude product is dissolved in ether and filtered through silica gel. The solvent is removed to yield the product.

EXAMPLE 11

4,5-dibromo-2-(2-pyridyl)imidazole

By the same procedure as example 9, 1.45 g (0.01 mol) 2-(2-pyridyl)imidazole is brominated. The crude product is dissolved in ether, filtered through silica gel and the solvent removed to yield the product.

EXAMPLE 12

4,5-dibromo-2-(4-fluorophenyl)imidazole

By the same procedure as example 9, 1.62 g (0.01 mol) 2-(4-fluorophenyl)imidazole is brominated. The crude product is dissolved in ether, filtered through silica gel and the solvent removed to yield the product.

TABLE I

Selected Imidazoles

| Compound | $R^1$ | $R^2$ | $R^3$ | M | M.P. | Composition | El't | Calc. | Found |
|---|---|---|---|---|---|---|---|---|---|
| 1 | Br | Br | $CF_3$ | H | 162–164 | $C_4HBr_2F_3N_2$ | C | 16.35 | 16.59 |
|   |   |   |   |   |   |   | H | 0.34 | 0.20 |
|   |   |   |   |   |   |   | Br | 54.38 | 54.20 |
|   |   |   |   |   |   |   | F | 19.39 | 19.05 |
|   |   |   |   |   |   |   | N | 9.53 | 9.51 |
| 2 | $CF_3$ | Br | Br | H | 174–179 | $C_4HBr_2F_3N_2$ | C | 16.34 | 17.14 |
|   |   |   |   |   |   |   | H | 0.34 | 0.34 |
|   |   |   |   |   |   |   | Br | 54.38 | 53.21 |
|   |   |   |   |   |   |   | F | 19.39 | 19.72 |
|   |   |   |   |   |   |   | N | 9.53 | 9.55 |
| 3 | Br | Br | $CF_3$ | Na | 100 | $C_4HBr_2F_3N_2Na$ ¼ $CH_3OH^*$ | C | 15.76 | 15.41 |
|   |   |   |   |   |   |   | H | 0.60 | 0.53 |
|   |   |   |   |   |   |   | Br | 48.48 | 48.30 |
|   |   |   |   |   |   |   | F | 17.20 | 18.03 |
|   |   |   |   |   |   |   | N | 8.48 | 8.41 |
|   |   |   |   |   |   |   | Na | 6.97 | 6.67 |
| 4 | Br | $CF_3$ | $CF_3$ | H | 125–127 | $C_5HBr_6F_2N$ | C | 21.22 | 20.99 |
|   |   |   |   |   |   |   | H | 0.36 | 0.33 |
|   |   |   |   |   |   |   | Br | 28.24 | 27.68 |
|   |   |   |   |   |   |   | F | 40.28 | 40.61 |
|   |   |   |   |   |   |   | N | 9.90 | 10.28 |
| 5 | Br | Br | $CF_3$ | $-COC_2H_5$ | oil | $C_7H_5Br_2F_3N_2O_2$ | C | 22.97 | 22.97 |
|   |   |   |   |   |   |   | H | 1.38 | 1.38 |
|   |   |   |   |   |   |   | Br | 43.67 | 43.55 |
|   |   |   |   |   |   |   | F | 15.58 | 15.24 |
|   |   |   |   |   |   |   | N | 7.56 | 8.04 |
| 6 | $CF_3$ | H | $CF_3$ | H | 126–143 | $C_5H_2F_6N_2$ | C | 29.42 | 29.73 |
|   |   |   |   |   |   |   | H | 0.99 | 1.04 |
|   |   |   |   |   |   |   | F | 55.77 | 52.81 |
|   |   |   |   |   |   |   | N | 13.73 | 13.46 |
| 7 | $CF_3$ | Br | $CF_3$ | H | 140–145 | $C_5HBrF_6N_2$ | C | 21.22 | 21.40 |
|   |   |   |   |   |   |   | H | 0.36 | 0.51 |
|   |   |   |   |   |   |   | Br | 28.24 | 28.51 |
|   |   |   |   |   |   |   | F | 40.28 | 37.15 |

TABLE I-continued

Selected Imidazoles

| Compound | R¹ | R² | R³ | M | M.P. | Composition | El't | Calc. | Found |
|---|---|---|---|---|---|---|---|---|---|
| | | | | | | | N | 9.90 | 9.62 |
| 8 | 3-Cl-phenyl | Br | $CF_3$ | H | 137–144 | $C_{10}H_5BrClF_3N_2$ | C | 36.89 | 37.62 |
| | | | | | | | H | 1.55 | 1.63 |
| | | | | | | | Br | 24.55 | 23.46 |
| | | | | | | | Cl | 10.89 | 10.95 |
| | | | | | | | F | 17.51 | 16.67 |
| | | | | | | | N | 8.61 | 8.80 |
| 9 | 3-Cl-phenyl | H | $CF_3$ | H | 186–187 | $C_{10}H_6ClF_3N_2$ | C | 48.70 | 48.62 |
| | | | | | | | H | 2.45 | 2.42 |
| | | | | | | | Cl | 14.38 | 14.11 |
| | | | | | | | F | 23.11 | 23.42 |
| | | | | | | | N | 11.36 | 11.28 |
| 10 | 3-pyridyl | H | $CF_3$ | H | 156–158 | $C_9H_6F_3N_2$ | C | 50.71 | 50.94 |
| | | | | | | | H | 2.84 | 2.85 |
| | | | | | | | N | 19.71 | 19.88 |
| | | | | | | | F | 26.74 | 26.54 |
| 11 | 5-Br-thienyl | H | $CF_3$ | H | 210–212 | $C_8H_4BrF_3N_2S$ | C | 32.34 | 33.32 |
| | | | | | | | H | 1.36 | 1.62 |
| | | | | | | | N | 9.43 | 9.19 |
| | | | | | | | Br | 26.90 | 23.70 |
| | | | | | | | F | 19.18 | 20.38 |
| 12 | 2,5-diCl-phenyl | H | $CF_3$ | H | 182–183 | $C_{10}H_5Cl_2F_3N_2$ | C | 42.73 | 43.49 |
| | | | | | | | H | 1.79 | 1.86 |
| | | | | | | | N | 9.97 | 9.77 |
| | | | | | | | Cl | 25.23 | 24.75 |
| | | | | | | | F | 20.28 | 20.00 |
| 13 | 3,5-diCl-phenyl | H | $CF_3$ | H | 193–194 | $C_{10}H_5Cl_2F_3N_2$ | C | 42.73 | 43.38 |
| | | | | | | | H | 1.79 | 1.86 |
| | | | | | | | N | 9.97 | 9.77 |
| | | | | | | | Cl | 25.23 | 24.75 |
| | | | | | | | F | 20.28 | 20.00 |
| 14 | 2,3-diCl-phenyl | H | $CF_3$ | H | 213–215 | $C_{10}H_5Cl_2F_3N_2$ | C | 42.73 | 43.05 |
| | | | | | | | H | 1.79 | 1.84 |
| | | | | | | | N | 9.97 | 9.95 |
| | | | | | | | Cl | 25.23 | 24.62 |
| | | | | | | | F | 20.28 | 20.70 |
| 15 | 4-Cl-3-$NO_2$-phenyl | H | $CF_3$ | H | 205–208 | $C_{10}H_5ClF_2N_3O_2$ | C | 41.18 | |
| | | | | | | | H | 1.73 | |
| | | | | | | | N | 14.41 | |
| | | | | | | | Cl | 12.16 | |
| | | | | | | | F | 19.55 | |
| 16 | 2-Cl-4-$NO_2$-phenyl | H | $CF_3$ | H | 195–198 | $C_{10}H_5ClF_3N_3O_2$ | C | 41.18 | 41.77 |
| | | | | | | | H | 1.73 | 1.77 |
| | | | | | | | N | 14.41 | 13.91 |
| | | | | | | | Cl | 12.16 | 12.13 |
| | | | | | | | F | 19.55 | 18.50 |
| 17 | 3-pyridyl | Br | $CF_3$ | H | 197–198 | $C_9H_5BrF_3N_3$ | C | 37.01 | 37.02 |
| | | | | | | | H | 1.73 | 1.74 |
| | | | | | | | N | 14.37 | 14.40 |
| | | | | | | | Br | 27.36 | 27.47 |
| | | | | | | | F | 19.52 | 19.19 |
| 18 | 5-Br-thienyl | Br | $CF_3$ | H | 193–200 | $C_8H_3Br_2F_3N_2S$ | C | 25.55 | 25.51 |
| | | | | | | | H | 0.80 | 0.81 |
| | | | | | | | N | 7.45 | 7.69 |
| | | | | | | | Br | 42.51 | 40.86 |
| | | | | | | | F | 15.16 | 15.13 |
| 19 | 2,5-diCl-phenyl | Br | $CF_3$ | H | 232–233 | $C_{10}H_4BrCl_2F_3N_2$ | C | 33.36 | 33.39 |
| | | | | | | | H | 1.12 | 1.11 |
| | | | | | | | N | 7.78 | 7.86 |
| | | | | | | | Br | 22.20 | |
| | | | | | | | F | 15.83 | 15.58 |
| 20 | 2,3-diCl-phenyl | Br | $CF_3$ | H | 150–152 | $C_{10}H_4BrCl_2F_3N_2$ | C | 33.36 | 33.74 |
| | | | | | | | H | 1.12 | 1.14 |
| | | | | | | | N | 7.78 | 7.68 |
| | | | | | | | Br | 22.20 | 21.90 |
| | | | | | | | Cl | 19.70 | 19.26 |
| | | | | | | | F | 15.83 | 15.68 |

TABLE I-continued

Selected Imidazoles

| Compound | R¹ | R² | R³ | M | M.P. | Composition | El't | Calc. | Found |
|---|---|---|---|---|---|---|---|---|---|
| 21 | 4-NO₂-C₆H₄-Cl | Br | CF₃ | H | 189–193 | $C_{10}H_4BrClF_2N_3O$ | C | 32.41 | 32.75 |
|  |  |  |  |  |  |  | H | 1.09 | 1.11 |
|  |  |  |  |  |  |  | N | 11.34 | 11.08 |
|  |  |  |  |  |  |  | Br | 21.57 | 21.07 |
|  |  |  |  |  |  |  | Cl | 9.57 | 9.38 |
|  |  |  |  |  |  |  | F | 15.38 | 14.76 |
| 22 | 3-Cl-C₆H₄-Cl | Br | CF₃ | H | 156–158 | $C_{10}H_4BrCl_2F_3N_2$ | C | 33.36 | 33.63 |
|  |  |  |  |  |  |  | H | 1.12 | 1.10 |
|  |  |  |  |  |  |  | N | 7.78 | 7.68 |
|  |  |  |  |  |  |  | Br | 22.20 | 21.90 |
|  |  |  |  |  |  |  | Cl | 19.70 | 19.55 |
|  |  |  |  |  |  |  | F | 15.83 | 16.10 |
| 23 | C₆F₅ | Br | CF₃ | H | 157–158 | $C_{10}HBrF_8N_2$ | C | 31.52 | 31.75 |
|  |  |  |  |  |  |  | H | 0.26 | 0.31 |
|  |  |  |  |  |  |  | N | 7.35 | 7.28 |
|  |  |  |  |  |  |  | Br | 20.97 | 20.43 |
|  |  |  |  |  |  |  | F | 39.89 | 40.62 |
| 24 | 2,4-Cl₂-C₆H₃ | Br | CF₃ | H | 193–195 | $C_{10}H_4BrCl_2F_3N_2$ | C | 33.36 | 33.66 |
|  |  |  |  |  |  |  | H | 1.12 | 7.15 |
|  |  |  |  |  |  |  | N | 7.78 | 7.67 |
|  |  |  |  |  |  |  | Br | 22.20 | 22.03 |
|  |  |  |  |  |  |  | F | 15.83 | 15.44 |
|  |  |  |  |  |  |  | Cl | 19.70 | 19.26 |
| 25 | 2-Cl-6-NO₂-C₆H₃ | Br | CF₃ | H | 177–178 | $C_{10}H_4BrClF_3N_3O_2C$ | C | 32.41 | 32.79 |
|  |  |  |  |  |  |  | H | 1.09 | 1.09 |
|  |  |  |  |  |  |  | N | 11.34 | 11.19 |
|  |  |  |  |  |  |  | Br | 21.57 | 21.09 |
|  |  |  |  |  |  |  | F | 15.38 | 14.87 |
|  |  |  |  |  |  |  | Cl | 9.57 | 9.45 |
| 26 | CH₃ | H | CF₃ | H | 175–176 | $C_5H_5F_3N_2$ | C | 40.00 | 39.72 |
|  |  |  |  |  |  |  | H | 3.36 | 3.32 |
|  |  |  |  |  |  |  | F | 37.97 | 39.42 |
|  |  |  |  |  |  |  | N | 18.67 | 19.65 |
| 27 | CH₃ | Br | CF₃ | H | 178–181 | $C_5H_4BrF_3N_2$ | C | 26.22 | 26.24 |
|  |  |  |  |  |  |  | H | 1.76 | 1.76 |
|  |  |  |  |  |  |  | Br | 34.90 | 34.30 |
|  |  |  |  |  |  |  | F | 24.59 | 24.40 |
|  |  |  |  |  |  |  | N | 12.23 | 11.99 |
| 28 | 2,5-Cl₂-C₆H₃ | Br | CF | H | 180–182 | $C_{10}H_4BrCl_3F_2N$ | C | 33.35 | 33.24 |
|  |  |  |  |  |  |  | H | 1.11 | 1.04 |
|  |  |  |  |  |  |  | Br | 22.21 | 20.74 |
|  |  |  |  |  |  |  | Cl | 19.71 | 21.47 |
|  |  |  |  |  |  |  | F | 15.84 | 15.64 |
|  |  |  |  |  |  |  | N | 7.78 | 7.63 |
| 29 | 2-Cl-C₆H₄ | Br | CF₃ | H | 110–112 | $C_{10}H_5BrClF_3N_2$ | C | 36.89 | 38.61 |
|  |  |  |  |  |  |  | H | 1.55 | 2.31 |
|  |  |  |  |  |  |  | Br | 24.55 | 20.83 |
|  |  |  |  |  |  |  | Cl | 10.89 | 10.74 |
|  |  |  |  |  |  |  | F | 17.51 | 16.28 |
|  |  |  |  |  |  |  | N | 8.61 | 8.03 |
| 30 | 2-F-C₆H₄ | Br | CF₃ | H | 110–112 | $C_{10}H_5BrF_4N_2$ | C | 38.85 | 39.26 |
|  |  |  |  |  |  |  | H | 1.62 | 1.60 |
|  |  |  |  |  |  |  | Br | 25.87 | 25.55 |
|  |  |  |  |  |  |  | F | 24.60 | 24.74 |
|  |  |  |  |  |  |  | N | 9.06 | 9.13 |
| 31 | 4-Cl-C₆H₄ | Br | CF₃ | H | 176–177 | $C_{10}H_5BrClF_3N_2$ | C | 36.89 | 36.86 |
|  |  |  |  |  |  |  | H | 1.55 | 1.46 |
|  |  |  |  |  |  |  | Br | 24.55 | 24.89 |
|  |  |  |  |  |  |  | Cl | 10.89 | 10.45 |
|  |  |  |  |  |  |  | F | 17.51 | 18.00 |
|  |  |  |  |  |  |  | N | 8.61 | 8.66 |
| 32 | 4-F-C₆H₄ | Br | CF₃ | H | 142–145 | $C_{10}H_5BrClF_3N_2$ | C | 38.85 | 38.84 |
|  |  |  |  |  |  |  | H | 1.62 | 1.55 |
|  |  |  |  |  |  |  | Br | 25.87 | 25.55 |
|  |  |  |  |  |  |  | F | 24.60 | 24.66 |
|  |  |  |  |  |  |  | N | 9.06 | 9.16 |
| 33 | 4-CF₃-C₆H₄ | Br | CF₃ | H | 177–180 | $C_{10}H_5BrF_4N_2$ | C | 36.78 | 37.11 |
|  |  |  |  |  |  |  | H | 1.39 | 1.39 |
|  |  |  |  |  |  |  | Br | 22.26 | 22.55 |
|  |  |  |  |  |  |  | F | 31.76 | 31.84 |
|  |  |  |  |  |  |  | N | 7.80 | 8.03 |

TABLE I-continued

Selected Imidazoles $$R^2\text{-}N\text{=}R^1$$ structure with $R^3$, $N$, $M$

| Compound | R¹ | R² | R³ | M | M.P. | Composition | El't | Calc. | Found |
|---|---|---|---|---|---|---|---|---|---|
| 34 | pyridyl (3-) | Br | CF₃ | H | 202–204 | C₉H₅BrF₃N₃ | C | 37.01 | 37.59 |
|  |  |  |  |  |  |  | H | 1.73 | 1.88 |
|  |  |  |  |  |  |  | Br | 27.36 | 24.76 |
|  |  |  |  |  |  |  | F | 19.52 | 19.96 |
|  |  |  |  |  |  |  | N | 14.37 | 14.42 |
| 35 | pyridyl (4-) | Br | CF₃ | H | 114–117 | C₉H₅BrF₃N₃ | C | 37.01 | 39.34 |
|  |  |  |  |  |  |  | H | 1.73 | 2.59 |
|  |  |  |  |  |  |  | Br | 27.36 | 15.84 |
|  |  |  |  |  |  |  | F | 19.52 | 20.84 |
|  |  |  |  |  |  |  | N | 14.37 | 13.77 |
| 36 | 2-F, 4-Cl-phenyl | Br | CF₃ | H | oil | C₁₀H₄BrClF₄N₂ | C | 34.95 | 32.83 |
|  |  |  |  |  |  |  | H | 1.16 | 1.07 |
|  |  |  |  |  |  |  | Br | 23.27 | 27.38 |
|  |  |  |  |  |  |  | Cl | 10.32 | 10.58 |
|  |  |  |  |  |  |  | F | 22.13 | 20.29 |
|  |  |  |  |  |  |  | M | 8.15 | 7.24 |
| 37 | 2-Cl, 4-F-phenyl | Br | CF₃ | H | 116–119 | C₁₀H₄BrClF₄N₂ | C | 34.95 |  |
|  |  |  |  |  |  |  | H | 1.16 |  |
|  |  |  |  |  |  |  | Br | 23.27 |  |
|  |  |  |  |  |  |  | Cl | 10.32 |  |
|  |  |  |  |  |  |  | F | 22.13 |  |
|  |  |  |  |  |  |  | M | 8.15 |  |
| 38 | 4-CN-phenyl | Br | CF₃ | H | 175–180 (dec) | C₁₁H₅BrF₃N₃ | C | 41.78 |  |
|  |  |  |  |  |  |  | H | 1.58 |  |
|  |  |  |  |  |  |  | Br | 25.29 |  |
|  |  |  |  |  |  |  | F | 18.04 |  |
|  |  |  |  |  |  |  | N | 8.86 |  |
| 39 | 4-OCH₃-phenyl | Br | CF₃ | H | 165–159 | C₁₁H₈BrF₃N₂O | C | 41.13 | 41.63 |
|  |  |  |  |  |  |  | H | 2.49 | 2.50 |
|  |  |  |  |  |  |  | Br | 24.90 | 23.78 |
|  |  |  |  |  |  |  | F | 17.76 | 17.13 |
|  |  |  |  |  |  |  | N | 8.72 | 8.82 |
|  |  |  |  |  |  |  | O |  |  |
| 40 | 4-Cl, 2-Br, NMe₂-phenyl | Br | CF₃ | H | 203–205 | C₁₀H₅Br₂ClF₃N₂ | C | 32.20 | 32.45 |
|  |  |  |  |  |  |  | H | 2.01 | 1.98 |
|  |  |  |  |  |  |  | Br | 35.73 | 34.19 |
|  |  |  |  |  |  |  | Cl | 7.93 | 8.32 |
|  |  |  |  |  |  |  | F | 12.74 | 12.51 |
|  |  |  |  |  |  |  | N | 9.39 | 9.46 |
| 41 | naphthyl | Br | CF₃ | H | 135–140 (dec) | C₁₄H₈BrF₃N₂ | C | 49.28 | 44.94 |
|  |  |  |  |  |  |  | H | 2.35 | 2.22 |
|  |  |  |  |  |  |  | Br | 23.44 | 29.58 |
|  |  |  |  |  |  |  | F | 16.72 | 13.42 |
|  |  |  |  |  |  |  | N³ | 8.21 | 7.41 |
| 42 | phenyl | Br | CF₃ | H | oil | C₁₀H₆BrF₃N₂ | C | 41.25 | 39.69 |
|  |  |  |  |  |  |  | H | 2.06 | 1.90 |
|  |  |  |  |  |  |  | Br | 27.47 | 33.45 |
|  |  |  |  |  |  |  | F | 19.59 | 17.91 |
|  |  |  |  |  |  |  | N | 9.62 | 9.62 |
| 43 | 2-Cl-pyridyl | Br | CF₃ | H |  | C₉H₄BrClF₃N₃ | C | 33.09 |  |
|  |  |  |  |  |  |  | H | 1.22 |  |
|  |  |  |  |  |  |  | Br | 24.52 |  |
|  |  |  |  |  |  |  | Cl | 10.88 |  |
|  |  |  |  |  |  |  | F | 17.46 |  |
|  |  |  |  |  |  |  | N | 12.87 |  |

*Analysis for CH₃OH not included.

The following data of Table II shows the herbicidal properties of the substituted imidazoles of the invention towards a number of common weeds. Using the procedure described below, substituted imidazoles were evaluated for control of the weeds listed below.

The following test procedure is employed. Seeds of selected crops and weeds are planted in soil in flats. For preemergence tests, the flats are treated with the test compound immediately after the planting. For postemergence tests, the seeds are allowed to germinate, and after two weeks the flats are treated with the test compound. The compound to be evaluated is dissolved in acetone, diluted with water, and sprayed over the flats using a carrier volume equivalent to 50 gallons per acre at the rate of application (pounds per acre, lb./A.) specified in the tables. About two weeks after the application of test compound, the state of growth of the plants is observed and the phytotoxic effect of the compound is evaluated. Table II gives the average percent control achieved by the test compounds in terms of the percent of the plants which are killed by the compounds.

TABLE II

| | | Biological Data | | | | | |
|---|---|---|---|---|---|---|---|
| | | Preemergent | | | Postemergent | | |
| | | rate | activity | | rate | activity | |
| | Compound Formula | (lb/A) | $M^a$ | $D^b$ | (lb/A) | $M^a$ | $D^b$ |
| 1 | 4,5-dibromo-2-Br, 4-CF₃ imidazole (NH) — Br, Br on ring, CF₃, N-H | 2 | 0 | 0 | 1 | 67 | 100 |
| 2 | imidazole with Br, Br, CF₃, N-H | 2 | 55 | 76 | 1 | 85 | 99 |
| 3 | imidazole with Br, Br, CF₃, N-Na | 2 | 42 | 53 | 1 | 73 | 100 |
| 4 | imidazole with CF₃, Br, CF₃ | 2 | 76 | 85 | 1 | 22 | 98 |
| 5 | imidazole with Br, Br, CF₃, N-C(O)C₂H₅ | 2 | 0 | 0 | 1 | 8 | 60 |
| 6* | imidazole with CF₃, CF₃, N-H | 2 | 0 | 0 | 1 | 0 | 0 |
| 7 | imidazole with Br, CF₃, CF₃, N-H | 2 | 63 | 93 | 1 | 48 | 84 |
| 10 | imidazole with CF₃, N-H, 2-pyridyl | 4 | 20 | 44 | 2 | 10 | 32 |
| 13 | imidazole with Cl, F₃C, N-H, 2,4-dichlorophenyl | 4 | 0 | 40 | 2 | 0 | 0 |
| 17 | imidazole with Br, F₃C, N-H, 2-pyridyl | 4 | 32 | 59 | 2 | 83 | 100 |
| 18 | imidazole with Br, F₃C, N-H, 5-bromo-2-thienyl | 4 | 40 | 19 | 2 | 66 | 100 |
| 19 | imidazole with Br, F₃C, N-H, 2,6-dichlorophenyl | 4 | 46 | 59 | 2 | 0 | 14 |

TABLE II-continued
| | | Biological Data | | | | | |
|---|---|---|---|---|---|---|---|
| | | | Preemergent | | | Postemergent | |
| | | rate | activity | | rate | activity | |
| | Compound Formula | (lb/A) | $M^a$ | $D^b$ | (lb/A) | $M^a$ | $D^b$ |
| 20 | 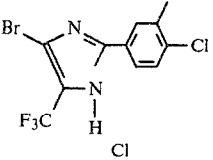 | 4 | 52 | 36 | 2 | 80 | 98 |
| 21 | 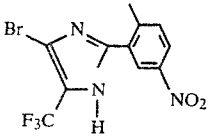 | 4 | 53 | 57 | 2 | 57 | 100 |
| 22 | 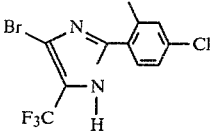 | 4 | 70 | 40 | 2 | 83 | 100 |
| 23 | 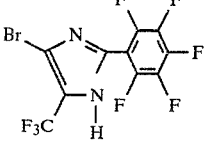 | 4 | 100 | 88 | 2 | 83 | 100 |
| 24 | 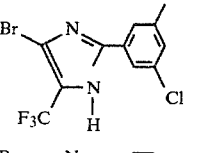 | 4 | 48 | 16 | 2 | 50 | 98 |
| 25 | 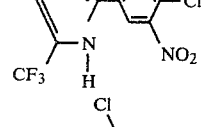 | 4 | 61 | 32 | 2 | 12 | 50 |
| 28 | 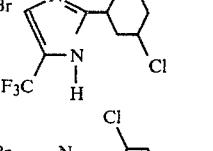 | 2 | 0 | 0 | 2 | 22 | 82 |
| 29 | 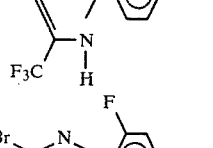 | 2 | 0 | 0 | 2 | 69 | 100 |
| 30 | 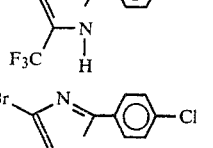 | 2 | 0 | 44 | 2 | 58 | 100 |
| 31 | 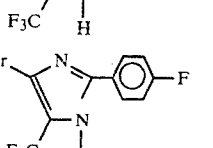 | 2 | 0 | 0 | 2 | 80 | 100 |
| 32 |  | 2 | 0 | 0 | 2 | 81 | 100 |

TABLE II-continued

Biological Data

| | | Preemergent | | | Postemergent | | |
|---|---|---|---|---|---|---|---|
| | | rate | activity | | rate | activity | |
| | Compound Formula | (lb/A) | $M^a$ | $D^b$ | (lb/A) | $M^a$ | $D^b$ |
| 33 | Br–C=N–C(C₆H₄–CF₃), F₃C–NH | 2 | 0 | 0 | 2 | 89 | 100 |
| 34 | Br–C=N–C(2-pyridyl), F₃C–NH | 2 | 0 | 0 | 2 | 0 | 0 |
| 35 | Br–C=N–C(3-pyridyl), F₃C–NH | 2 | 0 | 0 | 2 | 7 | 24 |
| 36 | Br–C=N–C(2-F,4-Cl-C₆H₃), F₃C–NH | 2 | 33 | 28 | 2 | 100 | 100 |
| 37 | Br–C=N–C(2-Cl,4-F-C₆H₃), F₃C–NH | 2 | 17 | 41 | 2 | 83 | 100 |
| 38 | Br–C=N–C(C₆H₄–CN), F₃C–NH | 2 | 0 | 0 | 2 | 0 | 80 |
| 39 | Br–C=N–C(C₆H₄–OCH₃), F₃C–NH | 4 | 0 | 0 | 4 | 18 | 40 |
| 40 | Br–C=N–C(2-Cl,4-NMe₂,5-Br-C₆H₂), F₃C–NH | 4 | 0 | 0 | 4 | 0 | 24 |
| 41 | Br–C=N–C(2-naphthyl), F₃C–NH | 4 | 0 | 0 | 4 | 0 | 0 |
| 42 | Br–C=N–C(C₆H₅), F₃C–NH | 4 | 0 | 0 | 4 | 72 | 100 |

TABLE II-continued

| | Biological Data | | | | | |
|---|---|---|---|---|---|---|
| | | Preemergent | | | Postemergent | |
| | rate | activity | | rate | activity | |
| Compound Formula | (lb/A) | $M^a$ | $D^b$ | (lb/A) | $M^a$ | $D^b$ |
| 43 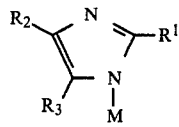 | 2 | — | — | 2 | — | — |

M and D are the average rate of kill for the enumerated weeds in each category.
$^a$M = monocots - barnyardgrass, downybrome, foxtail, yellow nutsedge, wildoats
$^b$D = dicots - cocklebur, marigold, morningglory, tomato, velvetleaf
*Although compound 6 exhibits no activity at the tested levels, it is expected that it will exhibit activity at higher rates of application.

Fungicidal evaluation of compounds of this invention is carried out by way of a foliar screening test. The general procedure for the fungicidal test is to take potted plants in proper condition of growth for susceptibility to the plant diseases to be evaluated, to spray these on a moving belt and allow them to dry. The plants are then inoculated with the respective fungal spores and allowed to incubate until the disease symptoms and the disease control are ready or estimated. Table III gives the results of the foregoing biological evaluations.

TABLE III

| | | Fungicidal Data | | | |
|---|---|---|---|---|---|
| Compound | Formula | Rate (PPM) | $BPM^c$ | $RB^c$ | $WSR^c$ |
| 4 | CF$_3$-N-Br / CF$_3$-N-H | 150 | — | — | A |
| 5 | Br-N-Br / CF$_3$-N-C(O)-C$_2$H$_5$ | 38 | A | — | A |
| 7 | Br-N-CF$_3$ / CF$_3$-N-H | 38 | A | — | — |
| 8 | Br-N-(C$_6$H$_4$Cl) / CF$_3$-N-H | 38 | — | A | B |

$^c$BPM - bean powdery mildew
RB - rice blast
WSR - wheat stem rust
$^d$Disease control: A = 97–100%; B = 90–96% control

We claim:

1. A compound of the formula

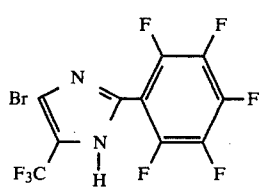

2. A herbicidal composition comprising an effective amount of a compound of the formula:

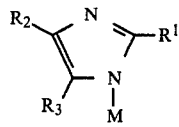

wherein $R^1$ is phenyl or naphthyl which may be substituted with up to 5 substituents selected from bromo, chloro, fluoro, trifluoromethyl, cyano, nitro, ($C_1$–$C_4$) alkyl, ($C_1$–$C_4$) alkylthio, ($C_1$–$C_4$) alkylsulfonyl, ($C_1$–$C_4$) alkylamino, or ($C_1$–$C_4$) dialkylamino; $R^2$ is selected from halo or trifluoromethyl; $R^3$ is trifluoromethyl and M is hydrogen or an alkali or alkaline earth metal in an agronomically acceptable carrier.

3. The herbicidal composition of claim 2 comprising an effective amount of compound wherein M is hydrogen, sodium, calcium, potassium or magnesium in an agronomically acceptable carrier.

4. The herbicidal composition of claim 2 comprising an effective amount of the compound in which $R^2$ is bromo and $R^3$ is trifluoromethyl in an agronomically acceptable carrier.

5. A herbicidal composition comprising an effective amount of a compound of the formula:

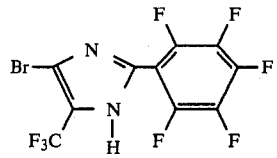

in an agronomically acceptable carrier.

6. A herbicidal composition comprising an effective amount of compound of the formula:

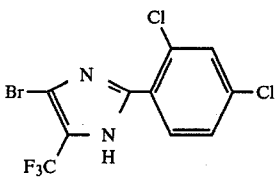

in an agronomically acceptable carrier.

7. A method of controlling undesirable plant growth which comprises applying to the area to be controlled, a composition according to claim 2, 3, 4, 5 or 6 in an amount sufficient to control the growth of the plants.

8. The method of claim 7 in which the composition is applied after the emergence of the plants from the growth medium.

9. The method of claim 7 in which the composition is applied to the growth medium in the area to be controlled prior to emergence of the plants from the growth medium.

10. The method of claim 7 wherein the compound is applied at a rate of about 0.1 to about 12 lbs./acre.

* * * * *